Figure 1:
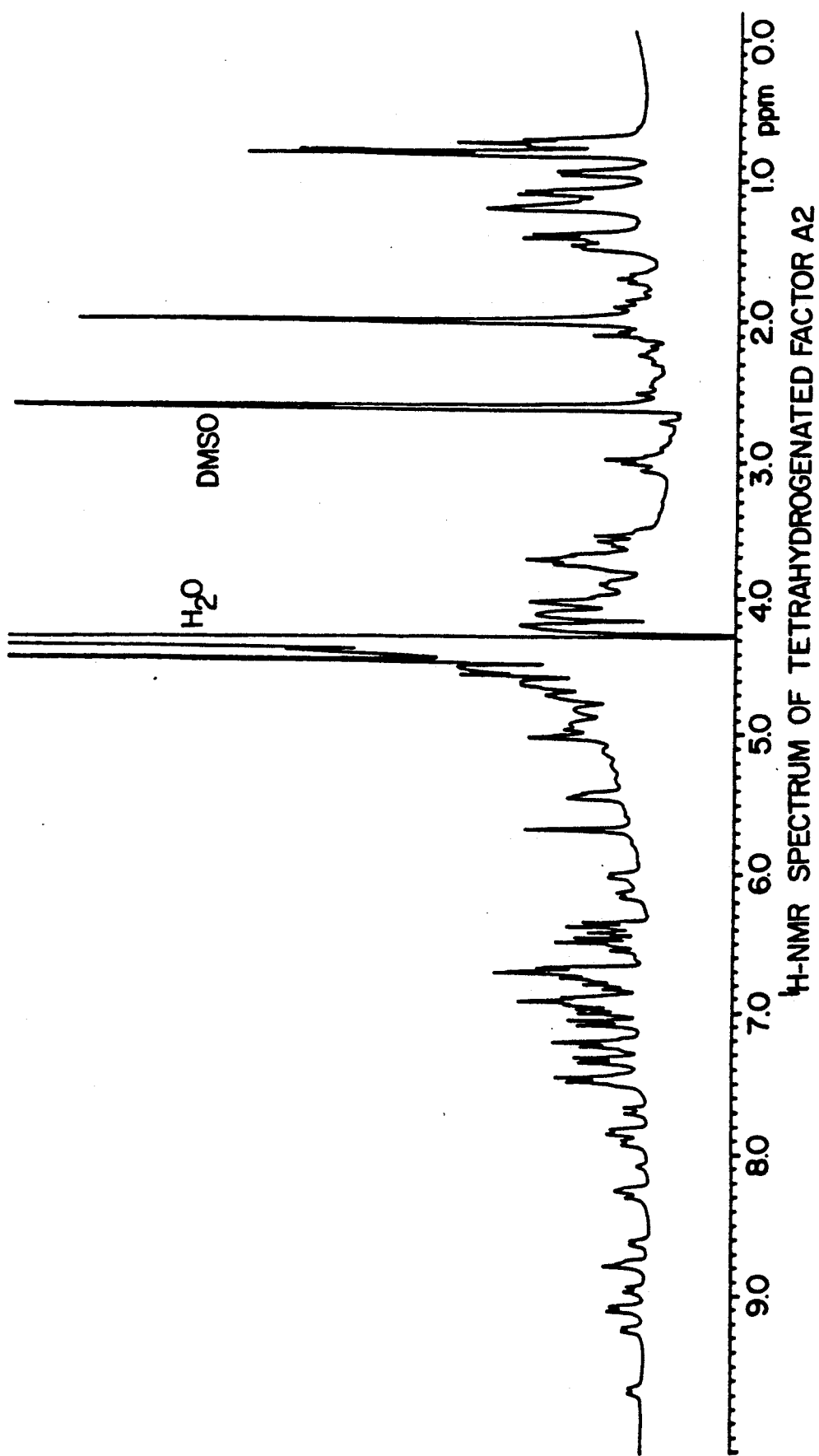

United States Patent [19]

Ciabatti et al.

[11] Patent Number: 5,108,988
[45] Date of Patent: Apr. 28, 1992

[54] HYDROGENATED DERIVATIVES OF ANTIBIOTIC A/16686

[75] Inventors: Romeo Ciabatti, Novate Milanese; Bruno Cavalleri, Milan, both of Italy

[73] Assignee: Gruppo Lepetit S.P.A., Milan, Italy

[21] Appl. No.: 280,035

[22] Filed: Dec. 5, 1988

[30] Foreign Application Priority Data

Dec. 23, 1987 [GB] United Kingdom ............... 8729989

[51] Int. Cl.$^5$ .................. A61K 37/02; C07K 7/56
[52] U.S. Cl. ................................ 514/11; 530/317
[58] Field of Search ............ 514/9, 10, 11; 530/317, 530/318, 319, 320, 321, 322

[56] References Cited

U.S. PATENT DOCUMENTS 4,303,646 12/1981 Cavalleri et al. .
4,427,656 1/1984 Cavalleri et al. .

FOREIGN PATENT DOCUMENTS 321696 6/1989 European Pat. Off. ............. 514/11

OTHER PUBLICATIONS

B. Cavalleri et al., *The Journal of Antibiotics*, vol. XXXVII No. 4, pp. 309–317, (1984).

*Primary Examiner*—C. Warren Ivy
*Assistant Examiner*—Celia Chang
*Attorney, Agent, or Firm*—J. Michael Dixon

[57] ABSTRACT

The invention concerns tetrahydroderivatives of factors A1, A2, A3, A'1, A'2, A'3 of antibiotic A/16686 and mixtures thereof. The tetrahydroderivatives are produced by hydrogenation of the above mentioned factors, preferably by catalytic hydrogenation.

The compounds have antibacterial activity, in particular, against widely diffused gram positive bacteria and are particularly useful for topical treatment of wound infections and acne.

11 Claims, 3 Drawing Sheets

UV SPECTRUM OF TETRAHYDROGENATED FACTOR A2

HYDROGENATED DERIVATIVES OF ANTIBIOTIC A/16686

The invention regards depsipeptidic compounds of the following structure formula I

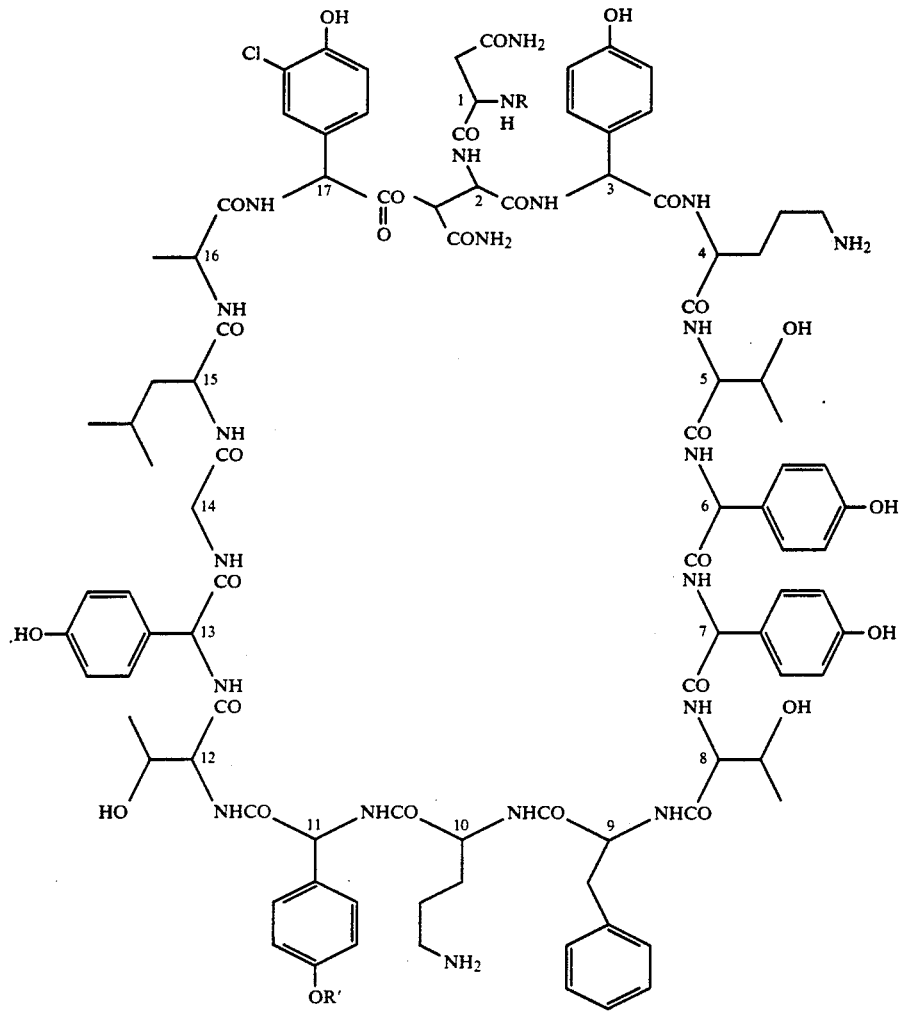

wherein:

R is: —CO—CH$_2$—CH$_2$—CH$_2$—CH$_2$—CH$_2$—CH$_2$—CH$_3$, —CO—CH$_2$—CH$_2$—CH$_2$—CH$_2$—CH$_2$—CH(CH$_3$)$_2$ or —CO—CH$_2$—CH$_2$—CH$_2$—CH$_2$—CH$_2$—CH$_2$—CH(CH$_3$)$_2$
and R' represents an alpha-D-mannopyranosyl rest or a 2-O-alpha-D-mannopyranosyl-alpha-D-mannopyranosyl rest and the acid addition salts thereof including their mixtures in any proportion, the process for their preparation and their use as antibiotics.

The above mentioned substances are correlated with antibiotic A/16686 and are produced by hydrogenation of the compounds identified as antibiotic A/16686 factors A1, A2, A3, A'1, A'2, and A'3 and the mixtures thereof.

Antibiotic A/16686 is a substance active against gram-positive bacteria described in U.S. Pat. No. 4,303,646 together with its manufacture process and pharmaceutical compositions containing it.

It was then found that three closely related components could be isolated from antibiotic A/16686 which were named factors A1, A2 and A3. Factor A2 ramoplanin is the component obtained in preponderant amount and is the most relevant for the biological activity, while factors A1 and A3 are obtained in a minor amount. These substances as well as their preparation and uses are described in U.S. Pat. No. 4,427,656.

A method for selectively enhancing the production of factors A2 and/or A3 of antibiotic A/16686 by adding appropriate precursors to an A/16686 producing culture is described in European Patent Application Publication No. 0259780. The co-pending European Patent Application Ser. No. 88116947.8 (corresponding to U.S. patent application Ser. No. 266,543 filed on Nov. 3, 1988) claiming priority of UK Ser. No. 8727807 of Nov. 27, 1987, describes the preparation of antibiotic A/16686 factors A'1, A'2 and A'3, whose structure corresponds to that of the compounds of formula I above wherein R' is an alpha-D-mannopyranosyl rest and R is:

—CO—CH=CH—CH=CH—CH$_2$—CH$_2$—CH$_3$,
—CO—CH=CH—CH=CH—CH$_2$—CH(CH$_3$)$_2$
or
—CO—CH=CH—CH=CH—CH$_2$—CH$_2$—CH(CH$_3$)$_2$.

The six compounds of this invention for the sake of brevity are identified also as (refer to formula I):

A/16686 tetrahydrogenated factor A1 (R:—CO(CH$_2$)$_6$CH$_3$; R': 2-O-alpha-D-mannopyranosyl-alpha-D-mannopyranosyl rest A/16686 tetrahydrogenated factor A2 (R:—CO(CH$_2$)$_5$CH(CH$_3$)$_2$; R': as above)

A/16686 tetrahydrogenated factor A3 (R:—CO(CH$_2$)$_6$CH(CH$_3$)$_2$; R' as above)

A/16686 tetrahydrogenated factor A'1 (R:—CO(CH$_2$)$_6$CH$_3$; R': alpha-D-mannopyranosyl rest)

A/16686 tetrahydrogenated factor A'2 (R:—CO(CH$_2$)$_5$CH(CH$_3$)$_2$; R': as above)

A/16686 tetrahydrogenated factor A'3 (R:—CO(CH$_2$)$_6$CH(CH$_3$)$_2$; R' as above)

The compounds of this invention may be produced by hydrogenating the corresponding factors A1, A2, A3, A'1, A'2 and A'3 or a mixture of two or more of them. Accordingly, the hydrogenation may be carried out either on the single factors or on any mixture of two or more of them such as for instance the A/16686 antibiotic complex produced by fermentation of Actinoplanes sp. ATCC 33076 (a strain which has been deposited with the permanent culture collection ATCC and is now freely available and accepted under Budapest Treaty as of Jan. 31, 1981) as described in U.S. Pat. No. 4,303,646. Further examples of mixtures of the A/16686 factors are those resulting from the method of European Patent Application Publication No. 0259780 whereby the ratio of the factor A2 and/or A3 is selectively increased during the fermentation process, or the mixtures containing the factors of both A and A' groups which are obtainable by fermentation of the above mentioned Actinoplanes sp. ATCC 33076 under appropriate conditions or by contacting the group A factors or a mixture thereof with the mycelium of the same strain for an appropriate period of time under proper conditions, according to the methods described in the above mentioned European Patent Application Ser. No. 88116947.8 (corresponding to U.S. patent application Ser. No. 266,543 filed on Nov. 3, 1988). In all cases mentioned above, the starting materials may be either in the form of a free base or in the form of an acid addition salt such as those disclosed in U.S. Pat. Nos. 4,303,646, 4,427,656 and in the co-pending European Patent Application Ser. No. 88116947.8 (corresponding to U.S. patent application Ser. No. 266,543 filed on Nov. 3, 1988) and the hydrogenated products mixture may be separated into the pure components corresponding to the tetrahydro compounds of this invention.

Although any type of hydrogenation process capable of saturating conjugated double bonds in an aliphatic chain without involving any further chemical modification of the remaining portions of the molecule(s) of the A/16686 starting material may be applied, catalytic hydrogenation (for instance, see: J. March, "Advanced Organic Chemistry: Reactions, Mechanisms and Structure" second edition, pp.707–715, McGraw-Hill Kogakusha Ltd, Tokyo, 1977) represent a preferred mode of manufacturing the compound of formula I above.

The hydrogenation catalysts of the process of the invention are generally selected from transition metals and their compounds. Both heterogeneous catalysts (for instance, see M. Freifelder, "Catalytic Hydrogenation in Organic Synthesis: Procedures and Commentary", John Wiley & Sons, New York, 1978; M. Freifelder, "Practical Catalytic Hydrogenation: Techniques and Applications", John Wiley & Sons, New York, 1976) and catalysts which are soluble in the reaction medium (for instance, see: James, "Homogeneous Hydrogenation", J. Wiley & Sons, New York, 1973; and F. J. McQuillin "Homogeneous Hydrogenation in Organic Chemistry", D. Reidel Publishing Co, Dordrecht, Holland, 1976) can be used, although heterogeneous catalysts are preferred for the reason that their use makes easier the recovery of the reaction products. Palladium and platinum on carriers (e.g., charcoal, calcium carbonate, barium sulfate and activated alumina), or platinum oxide are generally the most preferred catalysts. Actually, according one preferred embodiments of this invention, 5% to 10% palladium on charcoal and platinum oxide are advantageously employed as hydrogenation catalysts for the manufacture of the compounds of this invention from A/16686 starting materials.

The proportion between the substrate to be hydrogenated and the catalyst may vary considerably. In general, these substances are contacted, on a weight to weight basis, in a proportion from 0.1 : 1 to 1.5 : 1, (catalyst to substrate, w/w) depending also on the specific characteristics of the selected catalyst and the reaction conditions. Generally, a ratio between 0.5 : 1 and 1.2 : 1 (catalyst to substrate, w/w) is preferred.

With heterogeneous catalysts, the reaction solvent usually, is water, a water miscible polar organic solvent such as a (C$_{1-4}$)alkanol, a glycol, a polyglycol, a water soluble ether (e.g., 2-methoxyethanol, tetrahydrofurane, tetrahydropyran) and acetic acid or a mixture thereof.

Representative and preferred examples of (C$_{1-4}$)alkanols are methanol and ethanol. The preferred reaction solvent is usually selected from water, a mixture water/methanol or water/ethanol in a ratio from 20 : 80 to 30 : 70 (v/v) and 5% to 20% aqueous acetic acid.

When the hydrogenation reaction is carried out on mineral acid addition salt of the starting A/16686 compound, this latter is usually added to the selected solvent and the mixture is made acidic by addition of an aqueous solution of said mineral acid up to pH value of about 2.5–3.

With homogeneous non ionic catalysts such as, for example, chlorotris(triphenylphosphine)rhodium, the hydrogenation reaction can be carried out in an organic solvent or in a mixture of organic solvents (e.g., dimethylformamide, benzene or a mixture of benzene and a lower alkanol). With homogenous ionic catalysts such as, for example, pentacyanocobaltate, appropriate solvents may be water or water : lower alkanol mixtures.

The reaction pressure is generally an important parameter in the hydrogenation reactions. In general, it is related to the type and concentration of the hydrogenation substrate, the catalyst and the reaction temperature. In the present case, it may be between the ambient pressure and 5 atm (490332.5 Pa). In general, high yields are already obtained by operating at ambient pressure or with a slight hydrogen over-pressure (between the ambient pressure and 1.5 atm).

As for the reaction temperature, good results are usually obtained by operating at room temperature. Depending on the specific reaction conditions, i.e., type and concentration of the catalyst and solvent, it may be possible or convenient to use higher or lower temperatures.

As it may be appreciated by those skilled in the art, the reaction time varies depending on the substrate and the specific reaction conditions. In general the hydrogenation reaction is completed in 3 to 12 hours. In any case, the reaction course may be monitored by TLC or HPLC techniques as known in the art. For instance, samples may be drawn at intervals and assayed in order to determine when the reaction is complete. The reaction may then be stopped in order to prevent the negative consequence of a prolonged contact between the final product and the reaction mass. A complementary or alternative procedure for evaluating the reaction time and the end of the hydrogenation process is based on the measure of the absorption of hydrogen gas by the reaction mass, taking into account that each mole of starting A/16686 compound absorbs two moles of hydrogen gas.

Once the reaction is completed, the reaction product is isolated according to known per se techniques. Typically, the catalyst is separated by filtration. The recovered catalyst is washed thoroughly and the filtrates are combined. These liquids contain the reaction product which is then recovered and purified according to known methods such as evaporation, extraction with solvents, precipitation by addition of non-solvents, column chromatography and the like. Sometimes, it may be convenient to concentrate the filtrates to a small volume to precipitate the crude hydrogenation product. The isolation of the antibiotic substances of this invention from the crude hydrogenation product, their separation and purification is conducted according to known per se techniques which include extraction with solvents, precipitation from the obtained solution by addition of non-solvents or by changing the pH of the solution, partition chromatography, reverse-phase partition chromatography, ion-exchange chromatography, affinity chromatography, HPLC techniques and the like.

When the catalytic hydrogenation is carried out on a substrate consisting of a mixture of two or more of the factors A1, A2, A3, A'1, A'2, and A'3 and obtainment of the single tetrahydrogenated products is desired, the separation and purification is carried out, preferably, by using preparative HPLC methods. The preparative HPLC operations are usually conducted under conditions which are common to the separation and purification of the A/16686 antibiotic factors. Examples of said separation and purification operations can be found, for instance, in U.S. Pat. No. 4,427,656 where a C-18 alkyl silanized silicagel column and an eluent mixture of aqueous ammonium formate and acetonitrile is employed.

During the preparative HPLC, the eluted liquids from each injection are checked by analytical HPLC and those fractions enriched in the single A/16686 hydrogenated factor(s) are separated.

The fractions enriched in each of the above compounds are combined and concentrated to dryness under vacuum. If necessary, the respective solid residues are desalted by chromatography through a macroporous resin (e.g. XAD-2), and elution with an acidic solution. The solid product(s) resulting from concentration of the eluted solution(s) is/are freeze-dried to yield the respective pure product(s) under the form of mineral acid addition salt(s), e.g., the dihydrochloride(s). The above operation can be repeated one or more time when the purity of the resulting products is not satisfactory.

Antibiotic A/16686 tetrahydrogenated factors A1, A2 A3, A'1, A'2 and A'3 are submitted to sugar content determination (acid hydrolysis), acid/base titration, aminoacid analysis (for quantity and sequence), IR, UV, NMR spectrometry and Fast Atom Bombardment Mass Spectrometry (FAB-MS). The data resulting from these analytical tests confirm the assigned structures.

As shown in formula I the antibiotic substances of this invention possess two basic functions which can form acid addition salts according to conventional procedures.

Representative and suitable acid addition salts of the compounds of formula I include those salts formed by standard reactions with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like.

The transformation of the free amino or non-salt compounds of the invention into the corresponding addition salts, and the reverse, i.e., the transformation of an addition salt of a compound of the invention into the non-salt form, are within the ordinary technical skill and are encompassed by the present invention.

For instance, a compound of the invention can be transformed into the corresponding acid addition-salt by dissolving the non-salt form in an aqueous solvent and adding a slight molar excess of the selected acid. The resulting solution or suspension is then lyophilized to recover the desired salt.

In case the final salt is insoluble in a solvent where the non-salt form is soluble, the salt is recovered by filtration from the organic solution of the non-salt form after addition of the stoichiometric amount or a slight molar excess of the selected acid.

The non-salt form can be prepared from a corresponding acid salt dissolved in an aqueous solvent which is then neutralized to set free the non-salt form.

When following the neutralization desalting is necessary, a common desalting procedure may be employed.

For example, column chromatography on silanized silica gel, non-functionalized polystyrene, acrylic and controlled pore polydextrane resins (such as Sephadex LH 20) or activated carbon may be conveniently used. After eluting the undesired salts with an aqueous solution, the desired product is eluted by means of a linear gradient or a stepgradient of a mixture of water and a polar or apolar organic solvent, such as acetonitrile/water from 50:50 to about 100% acetonitrile.

As it is known in the art, the salt formation either with pharmaceutically acceptable acids or non-pharmaceutically acceptable acids may be used as a convenient purification technique. After formation and isolation, the salt form of an antibiotic of formula I above can be transformed into the corresponding non-salt or into a pharmaceutically acceptable salt.

The tetrahydrogenated factors of antibiotic A/16686 are particularly active against gram-positive microorganisms. The microbiological activity spectrum of antibiotic A/16686 tetrahydrogenated factor A2 is reported in the following Table:

TABLE I

| In vitro activity of A/16686 tetrahydrogenated factor A2 (dihydrochloride) | |
|---|---|
| Strain | MIC (mcg/ml) |
| Staphylococcus aureus Tour | 2 |
| Staphylococcus aureus Tour$^{a)}$ | 2 |
| Staphylococcus aureus Tour$^{b)}$ | 2 |
| Staphylococcus epidermidis ATCC 12228 | 1 |
| Staphylococcus haemolyticus L 602$^{c)}$ | 0.5 |

TABLE I-continued

| In vitro activity of A/16686 tetrahydrogenated factor A2 (dihydrochloride) | |
|---|---|
| Strain | MIC (mcg/ml) |
| Streptococcus pyogenes C203 SKF 13400 | 0.032 |
| Streptococcus pneumoniae UC41 | 0.032 |
| Streptococcus faecalis ATCC 7080 | 1 |
| Streptococcus mitis L 796[c] | 0.125 |
| Propionibacterium acnes ATCC 6922 | 0.125 |
| Propionibacterium acnes L 1557[c] | 0.125 |
| Propionibacterium acnes L 1559[c] | 0.125 |
| Propionibacterium acnes L 1563[c] | 0.125 |
| Propionibacterium acnes L 1565[c] | 0.125 |

[a] Inoculum $10^6$ cfµ/ml
[b] 30% bovine serum added
[c] Clinical isolates

Minimal Inibitory Concentration (MIC) is determined by either the broth or the agar serial two-fold dilution method. Culture media and growth conditions: Iso-Sensitest broth (Oxoid), for staphylococci and Streptococcus faecalis; Todd-Hewitt broth (Difco), for other streptococcal species; Wilkins-Chalgren agar for P.acnes (T. D. Wilkins, S. Chalgren: Antimicrob. Agents Chemother. 10, 926 (1976)); the final inoculum is of about $10^4$ colony-forming units/ml or spot. MIC is read as the lowest concentration which shows no visible growth after 18-24 hours incubation at 37° C.; for P. acnes the incubation is at 37° C. for 48 hours in anaerobic atmosphere ($N_2:CO_2:H_2$, 80:10:10). The acute toxicity of tetrahydrogenated A/16686 complex is determined in CD1 mice (Charles River) of both sexes weighing 18-22 g by a single i.v. injection of the product, solubilized in sterile saline. Infusion rate is 0.1 ml/second. The approximate $LD_{50}$ value is 170 mg/kg. The other compounds of this invention show biological activities comparable with that of A/16686 tetrahydrogenated factor A2.

The antibiotic compounds of this invention are useful for preparing medicaments against infections primarily due to gram-positive widely diffused bacteria. In particular, the compounds of this invention are useful for topical treatment of skin and wound infections and acne.

For general use as medicaments the compounds of this invention can be administered by different routes either in the form of free compounds or in the form of their addition salts with pharmaceutically acceptable acids, this latter form being preferred. The topical route is usually the most suitable way to administer the compounds of this invention.

For the medical uses the compounds of this invention are incorporated into pharmaceutical dosage forms suitable for oral, topical or parenteral administration such as tablets, capsules, lozenges, gelules, granules, powders, ointments, gels, liquid solutions, creams, solutions for injections, suspensions and the like. For instances, the formulations of said dosage forms can be carried out according to the general teaching of Remington's Pharmaceutical Sciences 17th Edition, 1985 Merck Publishing Company, Easton Pa.

The dosage unit may contain from 0.01 to 99 percent preferably from 0.5 to 80 percent of active ingredient. The daily dosage may depend on several factors such as body weight, the infecting microorganism, the severity of the infection, the age of the patient, the period and the way of administration. In general, the compounds of this invention are effective at a daily dosage ranging from about 2 mg to about 100 mg per kilogram of body weight, optionally divided into one or more administrations per day. Obviously, these dosages are only indicative and the most appropriate dosage can be adjusted in the specific cases and applications by relying on biological testings useful for determining the amount of active compound required to produced the desired effect.

The following Examples have the purpose to illustrate the invention but should not be construed as a limitation of its scope.

EXAMPLES

Example 1

Preparation of the tetrahydroderivative of A/16686 complex.

To a solution of 250 mg of A/16686 complex (obtained according to U.S. Pat. No. 4,303,646) in 25 ml of 10% $CH_3COOH$, 125 mg of 5% Pd/C are added. The solution is hydrogenated at room temperature and atmospheric pressure for 5 hours with magnetic stirring. After this period, further 125 mg of catalyst are added and the reaction is continued for additional 5 hours. At the end of the reaction a total of 5.4 ml of hydrogen is absorbed. The reaction mixture is filtered and the clear solution is freeze-dried to give 200 mg of the tetrahydroderivative of A/16686 complex.

Example 2

Preparation of the tetrahydroderivatives of A/16686 factors A1, A2, A3, A'1, A'2, and A'3.

A sample (9 grams) of a mixture of A/16686 factors containing factors A1, A2, A3, A'1, A'2, and A'3 in the same proportion as in the Example 4 of the co-pending European Patent Application Ser. No. 88116947.8 (corresponding to U.S. patent application Ser. No. 266,543 filed on Nov. 3, 1988), [i.e.: factors A1 (10%), A2(28%), A3(9%), A'1(10%), A'2(38%), A'3(5%); HPLC titers] is hydrogenated under the same conditions described in Example 1. The freeze-dried mixture of hydrogenated compounds (about 8 grams) is processed through a reverse phase preparative column (Lichrosorb RP-18, 10 micron 250 mm×50 mm, Merck) using as eluent a mixture of $CH_3CN:0.05M$ $HCOONH_4$ 4:6 at a flow rate of 12 ml/mm using an apparatus set up by assembling a Waters mod. 590 pump, and a Waters Lambda-Max mod 481LC UV detector (lambda=254 nm). The tetrahydroderivatives mixture is processed in runs of about 200 mg each dissolved in 5 ml of water. The fractions containing each of the factors are pooled, evaporated and desalted through a macroporous cross-linked polystyrene resin column (XAD-2, 80 cm×2.6 cm, Rohm and Haas) eluting first with water to eliminate the ammonium formate and then with a mixture $CH_3CN$ : HCl N/100 (1:1). The eluted fractions containing each of the tetrahydrogenated factors are evaporated and the residues are freeze-dried to yield the respective tetrahydrogenated factors of the title as the respective dihydrochlorides.

Example 3

Preparation of the tetrahydroderivative of antibiotic A/16686 factor A2 from antibiotic A/16686 factor A2.

To a solution of 1 g of antibiotic A/16686 factor A2 in 60 ml of N/1000 HCl (pH 3) 0.33 g of $PtO_2$ is added and the mixture is submitted to hydrogenation at room temperature and atmospheric pressure. After 7 hours, 80 ml of hydrogen are absorbed and the reaction is complete. Diatomaceous earth (celite 0.5 g) is added and the catalyst is filtered off by repeated filtrations on the same filter until a clear filtrate is obtained. The clear solution is filtered further on a 0.22 micron microporous filter (Millex®GC, Waters) to remove traces of the catalyst. The filtrate is freeze-dried to yield 0.82 g of the tetrahydroderivatives of antibiotic A/16686 factor A2. The same procedure can be followed for preparing the other tetrahydrogenated factors from the respective unsaturated compounds.

Example 4

Analytical assays and physico-chemical characterization.

4.1 Analytical HPLC

Apparatus: Hewlett-Packard liquid chromatograph, mod. 1084 B equipped with a UV detector set at 254 nm. Column: Erbasil C-18, 10 micron, 250 mm×4.6 mm (Carlo Erba).

| Mobile phase: | A) 0.05M $HCOONH_4$ | | | | | | |
|---|---|---|---|---|---|---|---|
| | B) $CH_3CN$ | | | | | | |
| Flow rate: | 0.8 ml/min | | | | | | |
| Gradient profile: | min | 0 | 10 | 21 | 27 | 30 | 32 |
| | % B | 34 | 35 | 40 | 46 | 50 | 34 |

Under these conditions the retention times ($t_R$) are as follows (the values of the respective non-hydrogenated compounds are reported between brackets):

| | $t_R$ (minutes) |
|---|---|
| Tetrahydro - A1 | 18.12 (11.63) |
| Tetrahydro - A2 | 23.40 (16.63) |
| Tetrahydro - A3 | 29.45 (22.40) |
| Tetrahydro - A'1 | 20.01 (13.01) |
| Tetrahydro - A'2 | 25.30 (18.62) |
| Tetrahydro - A'3 | 31.45 (24.29) |

4.2 Sugar analysis

Sugar determination is made after acid hydrolysis (2N $H_2SO_4$, 100° C., 2 hours) as described by B. Cavalleri et al. in The Journal of Antibiotics, Vol. 37, No. 4, pp 309–317, 1984. The presence of two D-mannose units for each molecule of the three hydrogenated factors A1, A2 and A3 and one D-mannose unit for each molecule of the three hydrogenated factors A'1, A'2 and A'3 is observed.

4.3 Amino acid analysis and $^1H$—NMR spectra

The acid hydrolysis is performed on the three tetrahydrogenated A1, A2 and A3 compounds with 6N HCl at 105° C. for 20 hours in a sealed tube. The mixture of amino acids is separated by column chromatography on a strongly acidic sulfonic divinylbenzene resin (Dowex 50 W) by eluting with aqueous HCl of increasing concentrations from 0.05N to 2N.

The amino acids are identified by comparison with authentic samples on the basis of $^1H$—NMR and GC—MS. The amino acid ratio and their sequence in the intact molecules are determined by NMR experiments.

All three compounds show the same amino acids compositions and sequence.

The following Table II shows the type and number of amino acid residues in each of the three tetrahydrogenated A factors.

The tetrahydrogenated A' factors have the same number of amino acid residues as it results from the hydrolysis carried out on the starting unsaturated compound reported in the co-pending European Patent Application Ser. No. 88116947.8 (corresponding to U.S. patent application Ser. No. 266,543 filed on Nov. 3, 1988).

TABLE II

| Amino acid | Number of units |
|---|---|
| Threo-beta-hydroxyaspartic acid | 1 |
| Aspartic acid | 1 |
| Allo-threonine | 3 |
| Glycine | 1 |
| Alanine | 1 |
| 4-Hydroxyphenylglycine | 5 |
| Leucine | 1 |
| Phenylalanine | 1 |
| 3-Chloro-4-hydroxyphenylglycine | 1 |
| Ornithine | 2 |

Two equivalents of ammonia per mole of each factor is titrated in the respective acid hydrolysis mixtures by means of an amino acid automatic analyzer providing evidence of two primary amide groups.

Furthermore, the total number of amidic nitrogen atoms (19) resulting from $^{15}N$ NMR experiments exceed by two the number of nitrogen atoms involved in the peptide bonds according to the number of amino acids in the molecule (Table II). Titration of the factors does not show any presence of free carboxylic groups. These considerations support that the two primary amide groups are on the aspartic and threo-betahydroxyaspartic acid units, respectively.

The NMR spectra are recorded in the temperature range from 25° to 60° C. on a Bruker AM 250 spectrometer equipped with an Aspect 3000 computer.

Standard pulse sequence and standard software are used for the 2D-NMR spectra, with slight modifications to suppress the water peak during the measurement.

The following 2D techniques are used: COSY, relayed COSY, double relayed COSY (W. J. Chazin, D. P. Goldenberg, T. E. Creighton, K. Wüthrich: Eur.J. Biochem., 152, 429–437 (1985)), COSY with enhancement of long range couplings (A. Bax, R. Freeman: J. Magn. Reson., 44, 542–561 (1981)), NOESY (S. Macura, K. Wüthrich, R. R. Ernst: J. Magn. Reson. 47; 351–357 (1982)) and COLOC (H. Kessler, C. Griesinger, J. Zarbock, H. R. Loosli: J. Magn. Reson. 57, 331–336 (1984)).

The following Table III shows the $^1H$-NMR chemical shifts (delta, ppm) of the amino acids of the amino acidic moiety of antibiotic A/16686 tetrahydrogenated factor A2 in $H_2O$ : DMSO, 4:1 at pH 4.6, temp. 40° C., internal standard TMS (delta=0.00 ppm).

TABLE III

| Amino acid | HN | $HC_{alpha}$ | $HC_{beta}$ | others |
|---|---|---|---|---|
| 1 Aspartic acid | 8.09 | 4.76 | 2.17, 1.62 | — |
| 2 Beta-hydroxy-aspartic acid | 8.41 | 5.49 | 5.69 | — |
| 3 4-Hydroxyphenyl-glycine | 9.84 | 6.21 | — | Phenyl 7.64(ortho), 7.02(meta) |
| 4 Ornithine | 9.20 | 4.21 | 2.04 | — |
| 5 Threonine | 7.56 | 4.36 | 4.03 | $HC_{gamma}$ 1.04 |
| 6 4-Hydroxyphenyl- | 8.91 | 5.44 | — | Phenyl 6.67(or- |

TABLE III-continued

| Amino acid | HN | HC$_{alpha}$ | HC$_{beta}$ | others |
|---|---|---|---|---|
| glycine | | | | tho), 6.45(meta) |
| 7 4-Hydroxyphenyl-glycine | 8.92 | 6.78 | — | Phenyl 6.82(ortho), 6.36(meta) |
| 8 Threonine | 8.24 | 3.71 | 3.92 | HC$_{gamma}$ 0.82 |
| 9 Phenylalanine | 7.74 | 4.97 | 2.04 | Phenyl 7.22(ortho), 6.92(meta, para) |
| 10 Ornithine | 7.59 | 4.20 | 2.18, 1.89 | HC$_{gamma}$ 1.67, HC$_{delta}$ 3.02 |
| 11 4-Hydroxyphenyl-glycine | 9.23 | 6.94 | — | Phenyl 7.34(ortho), 6.95(meta) |
| 12 Threonine | 9.06 | 4.72 | 3.94 | HC$_{gamma}$ 0.95 |
| 13 4-Hydroxyphenyl-glycine | 8.78 | 6.09 | — | Phenyl 7.08(ortho), 6.70(meta) |
| 14 Glycine | 7.89 | 3.76, 2.99 | — | — |
| 15 Leucine | 8.36 | 4.26 | 1.47 | HC$_{gamma}$ 1.47, HC$_{delta}$ 0.74 |
| 16 Alanine | 9.32 | 4.32 | 1.41 | — |
| 17 3-Chloro-4-hydroxyphenyl-glycine | 7.87 | 4.91 | — | Phenyl 6.83(ortho), 6.51(ortho), 6.36(meta) |

The $^1$H—NMR spectra relative to the amino acidic moiety of the other hydrogenated factors show the same pattern as the one of tetrahydrogenated factor A2.

FIG. 1 reports the $^1$H—NMR spectrum of tetrahydrogenated factor A2.

4.4 Fatty acid moieties

The hydrogenation of the conjugated double bonds of the fatty acid side chains is indicated by the absence of the vinylic proton resonance in the $^1$H—NMR spectra of the tetrahydrogenated factors registered under the experimental conditions described in Example 4.3.

4.5 Sugar

The D-mannose unit of the hydrogenated A' factors gives the following $^1$H—NMR signals (delta, ppm) for each of the three A' factors in H$_2$O: DMSO, 4:1 at pH 4.6, temperature 40° C., internal standard TMS (delta=0.00 ppm): 5.40 (one anomeric proton); 4.01, 3.91-3.71, 3.60-3.51 (other protons). The attachment point of the sugar to the peptidic moiety is determined by NMR experiments (Nuclear Overhauser Effect). For the hydrogenated A factors, the di-mannose unit gives the following $^1$H—NMR signals (delta, ppm) for each of them under the experimental conditions listed above: 5.68, 5.03 (two anomeric protons); 4.01; 3.91-3.71; 3.60-3.51 (other protons).

4.6 Lactone ring

The presence of a lactone ring is supported by the absorbance at 1760 cm$^{-1}$ in the IR spectrum (see under Example 5, paragraph 5.1). The position of the lactone bond is established by a) identification of the amino acid contributing to the lactone bond with its carboxylic group
b) identification of the hydroxy-amino acid contributing to the lactone bond with its hydroxyl group.

According to step a), finely ground CaCl$_2$ (2.5 g) is added to a cooled (0°-5° C.) solution of NaBH$_4$ (1.5 g) in absolute EtOH (150 ml) with magnetic stirring. After 1.5 hour, tetrahydrogenated factor A2 (1 g) dissolved in dry DMF (60 ml) is added dropwise. The cooled reaction mixture is stirred for 24 hours, then it is cautiously poured into water (600 ml). The pH is adjusted at 5 with aqueous HCl and the solution is desalted on a column filled with a macroporous cross-linked polystyrene resin XAD-2 (Amberlite Rohm and Haas) by eluting first with H20 to remove salts and after with a mixture 0.01N HCl:CH$_3$CN 1:1 to recover the reduced peptide. Fractions containing the peptide are combined and concentrated to dryness under vacuum.

The residue is hydrolyzed with 6N HCl at 105° C. for 20 hours. The acidic solution after extraction with ethyl acetate is concentrated under vacuum. The residue is chromatographed on a Dowex 50W×4 column by eluting with 0.05 N HCl. The fractions containing the wanted compound (checked by bidimensional HPTLC: cellulose, first run:butanol:acetic acid:water 4:1:5, upper layer, second run:pyridine:water 4:1; spots of amino acids are located by spraying with ninhydrin and heating at 120° C. for 5 minutes) are combined and concentrated. The oily residue is purified again by preparative thin layer chromatography (SiO$_2$, 5 mm thick, butanol:acetic acid:water 4:1:5, upper layer) to obtain the 2-amino-2-(3-chloro-4-hydroxyphenyl)ethyl alcohol: $^1$H-NMR (250 MHz, DMSO-d$_6$) delta, ppm 3.45 (m,CH, partly covered by the water signal), 3.38 (m,CH$_2$), 6.92 (d, CH-5), 7.11 (dd, CH-6, $^3$J=8.8 Hz), 7.32 (d, CH-2, $^4$J=2.5 Hz). The structure is further confirmed by comparison with an authentic sample prepared from 3-chloro-4-hydroxyphenylglycine (30 mg) which is converted into its methyl ester (MeOH, HCl) then reduced with Ca(BH$_4$)$_2$ following the procedure reported above.

Step b) is accomplished by first reacting tetrahydrogenated factor A2 with phenylisocyanate. This latter reacts with all the free hydroxyl and amino groups of the peptide giving urethanes and ureas, respectively, that are usually rather resistant to acid hydrolysis carried out, as described in Example 4, paragraph 3. The amount of hydroxyaspartic acid does not decrease, while the amounts of the other hydroxylated amino acids decrease, thus indicating that it is the amino acid involved in the lactone linkage with its hydroxyl group.

Accordingly, tetrahydrogenated factor A2 (100 mg) is dissolved in DMF (2 ml) and phenylisocyanate (300 microliters) is added. The reaction mixture is left at room temperature for 48 hours, quenched by adding H$_2$O (20 ml) and filtered. The solid compound is hydrolyzed and analyzed for its amino acid composition as described in Example 4, paragraph 3. This conclusion is further confirmed by the fact that hydrolysis carried out on the phenylisocyanate derivative of a factor A2 compound where the lactone ring has been previously opened by treatment with 0.1 N NaOH for 0.5 hour at room temperature followed by acidification with 0.1 N HCl, shows a sensible decrease of the amount of hydroxyaspartic acid.

The same experiments carried out with tetrahydrogenated factors A1 and A3 give corresponding results. As for the hydrogenated A' factors, it is relied on the data shown in the co-pending European Patent Application Ser. No. 88116947.8 (corresponding to U.S. patent application Ser. No. 266,543 filed on Nov. 3, 1988) concerning the corresponding unsaturated compounds.

Example 5

Figure 2:
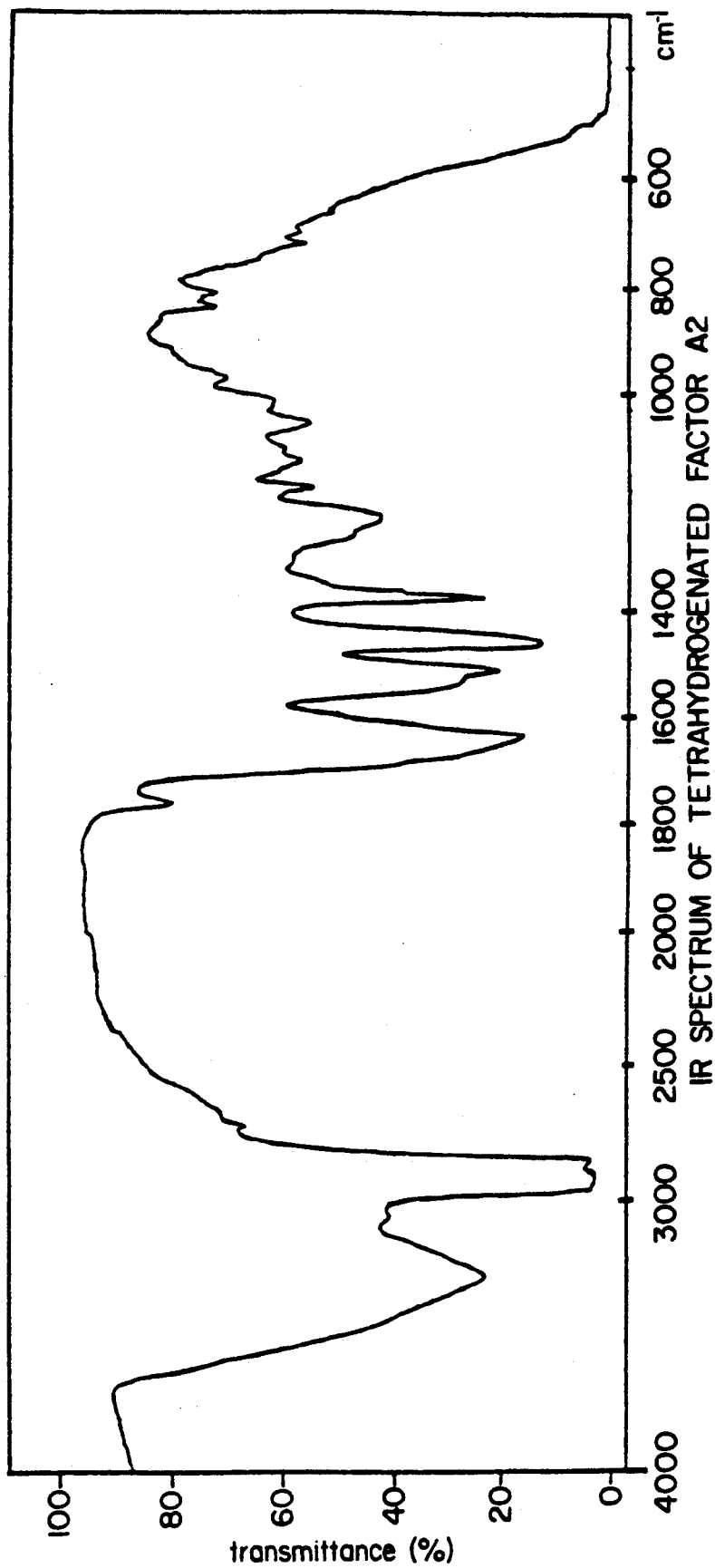

IR, UV and FAB-MS spectra 5.1 The IR spectrum of tetrahydrogenated factor A2 recorded as nujol mull with a Perkin-Elmer mod. 580 spectrophotometer is shown in FIG. 2 of the accompanying drawings. The following absorption maxima are observed: 3700-3100 (ny NH and ny OH), 3020-2800

(nujol), 1760 (ny C=O lactone), 1630 (ny C=O, amide I), 1510 (delta NH, amide II), 1460 and 1375 (nujol), 1230 (ny C—O, lactone), 1055—970 (ny C—O, sugars), 840 and 815 cm (gamma CH aromatics).

The spectra of the other hydrogenated factors do not show substantial differences.

Figure 3:
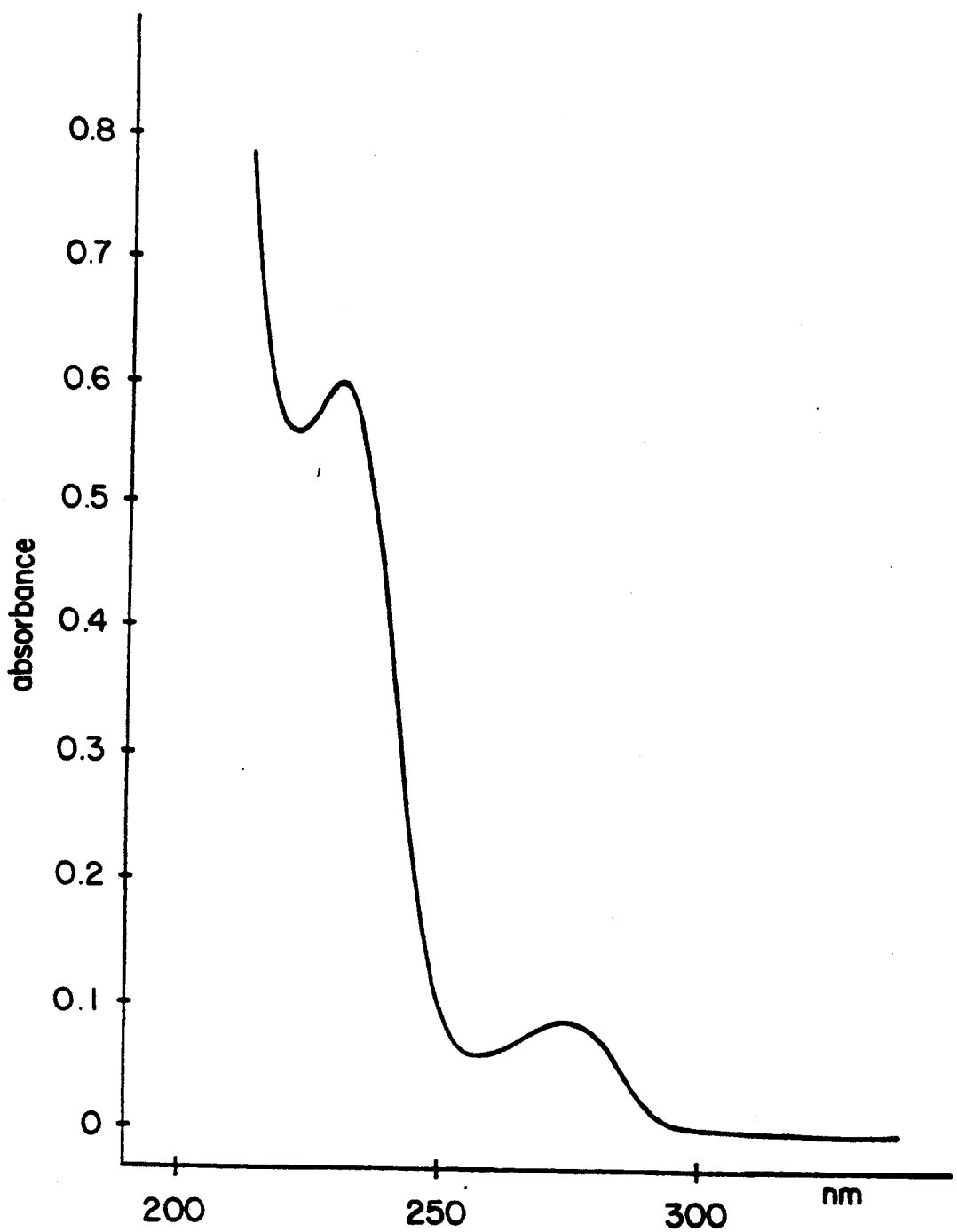

5.2 The Ultraviolet Spectrum of tetrahydrogenated factor A2 registered in water with a Perkin Elmer mod. 320 spectrophotometer is given in FIG. 3 of the accompanying drawings. The spectrum exhibits the following absorption maxima: 232 nm (E 1%, 1 cm 173.8 275 nm (E 1%, 1 cm 27.8).

The UV spectra of the other tetrahydrogenated factors do not show substantial differences.

5.3 The Fast Atom Bombardment Mass Spectra (FAB—MS) are recorded with a MS9/50TC instrument using a thioglycerol/glycerol 1:1 mixture as a matrix. Bombardment gas Xe; kinetic energy 6 keV; accelerating voltage 4 kV. The isotopic clusters of the cationized molecular ions MH+ indicate molecular weights of 2543 (tetrahydrogenated factor A1), 2557 (tetrahydrogenated factor A2) and 2571 (tetrahydrogenated factor A3), respectively, (lowest isotope compositions). These data, and the presence in the spectra of fragment ions corresponding to the loss of 325 microg. from the respective MH+ ions are in agreement with the structures assigned.

For the hydrogenated A' factors it is relied on the data shown in co-pending European Patent Application Ser. No. 88116947.8 (corresponding to U.S. patent application Ser. No. 266,543 filed on Nov. 3, 1988) concerning the corresponding unsaturated compounds.

5.4 Elemental analysis

The elemental analysis, after the sample has been previously dried at about 140° C. under inert atmosphere, give the following approximate percentage composition:

|       | Tetrahydrogenated factor A1, A'1 | | Tetrahydrogenated factor A2, A'2 | | Tetrahydrogenated factor A3, A'3 | |
| --- | --- | --- | --- | --- | --- | --- |
| C %   | 53.3 | 54.2 | 52.8 | 54.6 | 53.5 | 55.2 |
| H %   | 6.2  | 5.8  | 6.5  | 5.9  | 5.7  | 6.3  |
| N %   | 9.8  | 11.6 | 11.0 | 12.0 | 10.6 | 11.8 |
| Cl %  | 3.8  | 4.2  | 3.9  | 4.4  | 3.7  | 4.0  |
| ashes % | 1.3 | 0.7 | 0.5 | 0.9 | 1.2 | 0.7 |

The above values are in agreement with those calculated for the respective dihydrochloride salts of the six compounds.

We claim:

1. A compound of the formula [I]

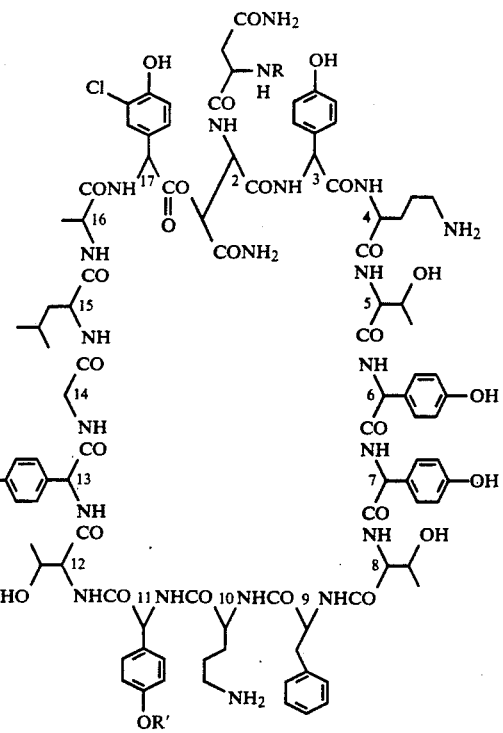

wherein:

R is: —CO—CH$_2$—CH$_2$—CH$_2$—CH$_2$—CH$_2$—CH$_2$—CH$_3$, —CO—CH$_2$—CH$_2$—CH$_2$—CH$_2$—CH$_2$—CH(CH$_3$)$_2$ or —CO—CH$_2$—CH$_2$CH$_2$—CH$_2$—CH$_2$—CH$_2$—CH(CH$_3$)$_2$ and R' represents an alpha-D-mannopyranosyl rest or a 2-0-alpha-D-mannopyranosyl-alpha-D-mannopyranosyl rest and the acid addition salts thereof including their mixtures in any proportion.

2. A compound of claim 1 wherein R is: —CO—CH$_2$—CH$_2$—CH$_2$—CH$_2$—CH$_2$—CH$_2$—CH$_3$, and R' is 2-O-alpha-D-mannopyranosyl-alpha-D-mannopyranosyl, 3. A compound of claim 1 wherein R is —CO—CH$_2$—CH$_2$—CH$_2$—CH$_2$—CH$_2$—CH(CH$_3$)$_2$ and R' is as in claim 2.

4. A compound of claim 1 wherein R is —CO—CH$_2$—CH$_2$—CH$_2$—CH$_2$—CH$_2$—CH$_2$—CH(CH$_3$)$_2$ and R' is as in claim 2.

5. A compound of claim 1 wherein R is as in claim 2 and R' is alpha-D-mannopyranosyl.

6. A compound of claim 1 wherein R is as in claim 3 and R' is alpha-D-mannopyranosyl.

7. A compound of claim 1 wherein R is as in claim 4 and R' is alpha-D-mannopyranosyl.

8. A compound of claim 1 in the form of the dihydrochloride.

9. A method for the treatment of infectious diseases in mammals comprising administering an antibacterially effective amount of a compound of claim 1 to the mammal in need thereof.

10. A method of claim 9 wherein the infectious disease is a wound infection or acne.

11. A pharmaceutical composition comprising a compound of claim 1 present in an antibacterially effective amount in admixture with a pharmaceutically acceptable carrier.

* * * * *